United States Patent [19]

Quallich

[11] Patent Number: 5,466,880
[45] Date of Patent: Nov. 14, 1995

[54] PROCESS FOR PREPARING KETONE ENANTIOMER

[75] Inventor: George J. Quallich, Stonington, Conn.

[73] Assignee: Pfizer Inc., New York, N.Y.

[21] Appl. No.: 244,832

[22] PCT Filed: Sep. 15, 1992

[86] PCT No.: PCT/US92/07654

§ 371 Date: Jun. 9, 1994

§ 102(e) Date: Jun. 9, 1994

[87] PCT Pub. No.: WO93/12062

PCT Pub. Date: Jun. 24, 1993

[51] Int. Cl.[6] .................................................. C07C 45/45
[52] U.S. Cl. ........................ 568/319; 560/51; 560/55; 560/101; 562/459; 558/51
[58] Field of Search ................. 560/5, 101, 55; 562/459; 558/51; 568/319

[56] References Cited

U.S. PATENT DOCUMENTS

| | | | |
|---|---|---|---|
| 4,556,676 | 12/1985 | Welch et al. | 514/554 |
| 4,777,288 | 10/1988 | Quallich et al. | 562/491 |
| 4,921,999 | 5/1990 | O'Brien | 560/52 |

Primary Examiner—James H. Reamer
Attorney, Agent, or Firm—Peter C. Richardson; Paul H. Ginsburg

[57] ABSTRACT

A novel multi-step process for preparing the (4S)-enantiomer of 4-(3,4-dichlorophenyl)-3,4-1(2H)- naphthalenone in a highly-optically pure form is disclosed. The process involved starts from the known 4-(3,4-dichlorophenyl)-4-ketobutanoic acid and proceeds through such intermediates as (1) isopropyl or tert.- butyl 4-(3,4-dichlorophenyl)-4-ketobutanoate, (2) isopropyl or tert.-butyl 4-(3,4-dichlorophenyl)-(4R)-hydroxybutanoate, (3) isopropyl or tert.-butyl 4-(3,4-dichlorophenyl)-(4R)-sulfonyloxybutanoate, (4) isopropyl or tert.-butyl 4-(3,4-dichlorophenyl)-(4R)-phenylbutanoate to finally yield the desired (4S)-4-(3,4-dichlorophenyl)-3,4-dihydro-1(2H)-naphthalenone compound in a highly-optically pure form. The latter compound, which is a (4S)-enantiomer per se, has utility as an intermediate that ultimately leads to pure cis-(1S)(4S)-N-methyl-4-(3,4-dichlorophenyl)-1,2,3,4-tetrahydro-1-naphthaleneamine (sertraline), which is a known antidepressant agent. The aforementioned isopropyl and tert.-butyl esters of 4-(3,4-dichlorophenyl)-(4R)-hydroxybutanoic acid, as well as their corresponding (4R)-methanesulfonyl, (4R)-benzenesulfonyl and (4R)-p-toluenesulfonyl derivatives, are all novel compounds, as are the aforementioned isopropyl and tert.-butyl esters of 4-(3,4-dichlorophenyl)-(4R)-phenylbutanoic acid as well as the aforesaid acid per se. These novel chiral compounds are all useful as key intermediates in the overall process of the present invention.

25 Claims, No Drawings

PROCESS FOR PREPARING KETONE ENANTIOMER

TECHNICAL FIELD

This application is a 371 of PCT U.S. 92/07,654 filed Sep. 15, 1992.

This invention relates to a new and useful process for preparing a ketone enantiomer. More particularly, it is concerned with a novel multi-step process for preparing the (4S)-enantiomer of 4-(3,4-dichlorophenyl)-3,4-dihydro-1(2H)-naphthalenone in a highly-optically pure form. The latter compound, which is a novel (4S)-enantiomer per se, has utility as a key intermediate that ultimately leads to the production of pure cis-(1S)(4S)-N-methyl-4-(3,4-dichlorophenyl)-1,2,3,4-tetrahydro-1-naphthaleneamine (sertraline), which is a known antidepressant agent. The invention also includes within its scope certain other novel compounds which are useful as intermediates in the various stages of the overall process.

BACKGROUND ART

There is described in U.S. Pat. Nos. 4,536,518 and 4,556,676 to W. M. Welch, Jr. et al., as well as in the paper of W. M. Welch, Jr. et al., appearing in the *Journal of Medicinal Chemistry*, Vol. 27, No. 11, p. 1508 (1984), a multi-step method for synthesizing pure racemic cis-(1S)(4S)-N-methyl-4-(3,4-dichlorophenyl)-1,2,3,4-tetrahydro-1-naphthaleneamine, starting from the readily available 3,4-dichlorobenzophenone and proceeding via the known racemic or (±)-4-(3,4-dichlorophenyl)-4-butanoic acid and then to (±) -4-(3,4-dichlorophenyl)-3,4-dihydro-1(2H)-naphthalenone (see also U.S. Pat. Nos. 4,777,288 and 4,839,104 to G. J. Quallich et al. for improved methods leading to these intermediates), with the latter ketone then being condensed with methylamine in the presence of titanium tetrachloride to yield N-[4-(3,4-dichlorophenyl)-3,4-dihydro-1(2H)-naphthalenylidene] methanamine. In the last step of the overall synthesis, the aforementioned imine is then readily reduced by means of catalytic hydrogenation or by the use of a metal hydride complex to yield N-methyl-4-(3,4-dichlorophenyl)-1,2,3,4-tetrahydro-1-naphthaleneamine, which is actually a mixture of the cis- and trans-isomers in the form of a racemate. The aforesaid isomeric mixture is then separated into its component parts by conventional means, e.g., by fractional crystallization of the hydrochloride salts or by column chromatography on silica gel of the corresponding free base. Resolution of the separated cis-racemate free base compound while in solution with an optically-active selective precipitant acid, such as D-(-)-mandelic acid, in a classical manner then ultimately affords the desired cis-(1S)(4S)-enantiomer (sertraline).

Nevertheless, the above described production of pure cis-(1S)(4S)-N-methyl-4-(3,4-dichlorophenyl)-1,2,3,4-tetrahydro-1-naphthaleneamine (sertraline) is disadvantageous in that equal amounts of the unwanted cis -(1R)(4R)-enantiomer are co-produced and must eventually be discarded, thereby lowering the overall yield of the desired cis-(1S)(4S)-enantiomer and increasing the total costs of production.

In accordance with the prior art, other asymmetric methods of induction (e.g., asymmetric syntheses) have been employed in the past with variable success in the field of organo-metallic chemistry to stereoselectively convert (and thereby resolve) other specific substrates. For instance, in a paper by W. M. Whitesides et al., appearing in the *Journal of the American Chemical Society*, Vol. 91, No. 17, p. 4871 (1969), as well as in an article by K. Mori et al., as reported in *Synthesis*, p. 752 (1982), there are described certain copper-assisted coupling reactions of various organic halides and tosylates that illustrate non-benzylic $S_N2$ displacement with cuprates at a secondary position in the substrate molecule. Additionally, B. H. Lipshutz et al., in the *Journal of Organic Chemistry*, Vol. 49, p. 3928 (1984), refer to various substitution reactions of secondary organic halides and epoxides with higher order, mixed organocuprates from both a synthetic and stereochemical point of view. They specifically report that the diphenyl(cyano)cuprate reagent of the formula $(\phi)_2Cu(CN)Li_2$ routinely displaces secondary organic bromides and iodides with 1.5 equivalents of said reagent, while the corresponding mesylates and tosylates are far less prone to such type substitution and generally do not lend themselves to the formation of acceptable yields of desired product unless amounts as high as ten equivalents of said displacement reagent are employed in the reaction.

However, this background study of the prior art would not be complete without also stating that B. H. Lipshutz et al., in the *Journal of the American Chemical Society*, Vol. 104, p. 4696 (1982), do report on chirality transfer when higher order cuprates if the formula $(\phi)_2Cu(CN)Li_2$ are reacted with bromides; while G. M. Whitesides et al., in the *Journal of the American Chemical Society*, Vol. 91, No. 17, p. 4871 (1969) and C. R. Johnson et al., in the *Journal of the American Chemical Society*, Vol. 95, No. 23, p. 7783 (1973), both report on chirality transfer when lower order cuprates of the formula $(\phi)_2CuLi$ are reacted with bromides and tosylates, respectively. This is best summarized in the review article by B. H. Lipshutz et al., appearing in *Tetrahedron*, Vol. 40, No. 24, p. 5005 (1984), where the anomolous behavior of the phenyl lithium-derived cuprates is also reported. Nevertheless, there is no known instance of clean $S_N2$ reactions occurring in secondary benzylic systems with either lower or higher order cuprates, although C. R. Johnson et al., in the *Journal of the American Chemical Society*, Vol. 95, No. 23, p. 7777 (1973), do report that a benzylic tosylate is displaced by the lower order diethyl cuprate without mention of chirality transfer. The Lipshutz et al. review article concludes that substitution reactions appearing at secondary centers are limited to those cuprates that are prepared from n-alkyl or vinyl precursors.

DISCLOSURE OF THE INVENTION

In accordance with the present invention, there is now provided a new and especially useful process for preparing the (4S)-enantiomer of 4-(3,4-dichlorophenyl)-3,4-dihydro-(1(2H)-naphthalenone in a highly-optically pure form by employing a novel, multi-step series of reactions, starting from the known 4-(3,4-dichlorophenyl)-4-ketobutanoic acid. More particularly, the novel process of this invention comprises a sequential series of steps that involve:

(a) first esterifying 4-(3,4-dichlorophenyl)-4-ketobutanoic acid with isopropylene or isobutylene in a reaction-inert aprotic organic solvent in the presence of an acidic catalyst to form the corresponding isopropyl or tert.-butyl 4-(3,4-dichlorophenyl)-4-ketobutanoate;

(b) reducing the 4-ketobutanoic acid ester obtained in step (a) with an appropriate asymmetric carbonyl reducing agent in a reaction-inert polar or non-polar aprotic organic solvent at a temperature ranging from about −15° C. up to about 40° C., until the reduction reaction to form the desired chiral isopropyl or tert.-butyl 4-(3,4-dichlorophenyl)-(4R)-hydroxybutanoate intermediate is substantially complete;

(c) sulfonylating the (4R)-hydroxybutanoic acid ester compound formed in step (b) with an organic sulfonyl halide of the formula RX, wherein R is methanesulfonyl, benzenesulfonyl or p-toluenesulfonyl and X is chlorine or bromine, in a reaction-inert organic solvent at a temperature ranging from about −20° C. up to about 40° C. in the presence of a standard base to yield the corresponding isopropyl or tert.-butyl 4-(3,4-dichlorophenyl)-(4R)-sulfonyloxybutanoate;

(d) subjecting the (4R)-sulfonyloxybutanoic acid ester obtained in step (c) to a copper-coupling reaction with dilithium diphenyl(cyano)cuprate of the formula $\phi_2Cu(CN)Li_2$ in a cyclic or lower dialkyl ether at a temperature ranging from about −80° C. up to about 20° C. to effect a stereochemical displacement of the organic (4R)-sulfonyloxy group of the (4R)-sulfonyloxybutanoic acid ester by the phenyl group of the dilithium diphenylcuprate reagent and so selectively form the corresponding isopropyl or tert.-butyl 4-(3,4 -dichlorophenyl)-(4R)-phenylbutanoate; and (e) thereafter cyclizing the stereospecific (4R)-phenylated n-butanoic acid ester product of step (d) in a reaction-inert aprotic organic solvent in the presence of a protic or Lewis acid catalyst at a temperature ranging from about −20° C. up to about 180° C. to finally yield (via the 4 -(3,4-dichlorophenyl)-(4R)-phenylbutanoic acid intermediate that is first formed in situ) the desired (4S)-4-(3,4 -dichlorophenyl)-3,4-dihydro-1(2H)-naphthalenone compound in a highly optically-pure form and in a high yield.

In this way, a compound such as 4-(3,4-dichlorophenyl) -4-ketobutanoic acid is readily converted in the form of an isopropyl or tertiary-butyl ester, via the novel chiral ester intermediates, viz., isopropyl or tert.-butyl 4-(3,4 -dichlorophenyl)-(4R)-hydroxybutanoate and the (4R)-methanesulfonyl, benzenesulfonyl and (4R)-p-toluenesulfonyl derivatives thereof, to the corresponding novel chiral isopropyl or tert.-butyl 4-(3,4-dichlorophenyl)-(4R)-phenylbutanoates, respectively, and ultimately to the novel (4S)-enantiomer final product, viz., (4S)-4-(3,4 -dichlorophenyl)-3,4-dihydro-1(2H)-naphthalenone, in a most facile manner. As previously indicated, the latter-named final product is useful as a valuable intermediate in the asymmetric synthesis of the antidepressant agent known as sertraline, which is cis-(1S)(4S)-N-methyl-4-(3,4 -dichlorophenyl)-1,2,3,4-tetrahydro-1-naphthaleneamine [see aforementioned U.S. Pat. Nos. 4,536,578, 4,777,288 and 4,839,104, as well as the *Journal of Medicinal Chemistry*, Vol. 27, No. 11, p. 1508 (1984), for the total synthesis of the corresponding racemic compound and its subsequent conversion into sertraline].

Accordingly, there is also included within the purview of this invention the novel chiral ester and acid intermediates used in the process, as well as the novel final product so obtained, and this includes, in addition to the aforementioned (4S)-4-(3,4-dichlorophenyl)-3,4-dihydro -1(2H)-naphthalenone final product, its immediate precursor, viz., the penultimate intermediate product known as 4-(3,4 -dichlorophenyl)-(4R)-phenylbutanoic acid and such esters as the isopropyl or tert.-butyl esters of 4-(3,4 -dichlorophenyl)-(4R)-phenylbutanoic acid that lead directly to said acid and then to said final product, as well as the isopropyl or tert.-butyl esters of 4-(3,4-dichlorophenyl) -(4R)-hydroxybutanoic acid and the corresponding (4R)-methanesulfonyl, benzensufonyl and (4R)-p-toluenesulfonyl derivatives thereof. The latter group of esters, of course, lead directly to the corresponding (4R)-phenylbutanoate ester derivatives as previously discussed. The preferred group of esters for the present purposes at hand are clearly the tertiary-butyl group of esters and this would specifically include such individual preferred member esters as tert.-butyl 4-(3,4-dichlorophenyl)-(4R)-hydroxybutanoate, tert.-butyl 4-(3,4-dichlorophenyl)-(4R) -methanesulfonyloxybutanoate and tert.-butyl 4-(3,4 -dichlorophenyl)-(4R)-phenylbutanoate, in view of what has already been discussed above.

DETAILED DESCRIPTION

In accordance with the process of this invention, the initial stage of the multi-step synthesis for producing the desired (4S)-4-(3,4-dichlorophenyl)-3,4-dihydro-1(2H)-napthalenone compound involves first esterifying the known 4-(3, 4-dichlorophenyl)-4-ketobutanoic acid in step (a) with isopropylene or isobutylene in a reaction-inert aprotic organic solvent to form the corresponding isopropyl or tert.-butyl 4-(3,4-dichlorophenyl)-4-ketobutanoate. This step is readily accomplished by first dissolving the aforementioned acid in a suitable reaction-inert aprotic organic solvent and then contacting the latter organic system with an excess in moles of gaseous isopropylene or isobutylene with respect to the 4-(3,4-dichlorophenyl)-4-ketobutanoic acid starting material in the presence of an acidic catalyst to form the desired ester. Preferred reaction conditions generally call for the presence of at least about twenty moles of isopropylene or isobutylene per one mole of organic acid starting material, with the most preferred range being from about 20:1 to about 30:1, in order to effect the desired branched-chain ester formation previously indicated. The acid catalyst that is called for is preferably a strong acid that is generally employed in catalytic amounts, e.g., at least about 0.5% by volume of acid catalyst based on the total volume of organic solvent employed. Most preferably, the acid catalyst is present at a level that ranges from about 0.5% up to about 5.0% by volume of the total amount of organic solvent employed in the reaction. Although it is usually preferable to employ concentrated sulfuric acid as the key acid catalyst for the reaction, other strong acids may also be used in this connection and these would preferably include strong mineral acids like hydrofluoric acid, hydrochloric acid and hydrobromic acid, as well as strong organic acids such as methanesulfonic acid and p-toluenesulfonic acid and even Lewis acids such as boron trifluoride and cuprous chloride, etc. By reaction-inert organic solvents as used herein is meant an organic solvent which dissolves the reactants, but does not react with same under the reaction conditions described. Preferred reaction-inert aprotic organic solvents for use in this connection include lower dialkyl ethers such as diethyl ether, di-isopropyl ether and di-n-butyl ether, cyclic ethers such as tetrahydrofuran and dioxane, aromatic hydrocarbons such as benzene, toluene and xylene and their halogenated derivatives like bromobenzene and 1,2-dichlorobenzene, as well as chlorinated lower hydrocarbons such as methylene chloride, ethylene dichloride, chloroform, trichloroethylene, s-tetrachlorethane and carbon tetrachloride, etc. According to one preferred embodiment of this particular reaction step, the reaction-inert aprotic organic solvent system may also contain a minor amount of the branched-chain alkanol corresponding to the desired ester final product, i.e., either isopropanol or tert.-butanol, as the case may be, to serve as a "spike" for the aforesaid aprotic organic solvent system. Preferred minor amounts of branched-chain alkanol ($C_3$-$C_4$) for use in this particular connection will range from about 0.5% up to about 5.0% by volume of the total amount of solvent employed. In general, the ester-formation step of this invention is usually carried out in the hereinbefore discussed solvent system at a temperature that ranges from about 0° C. up to about 50° C. and at a pressure that is at least about atmospheric, until the condensation reaction to form the desired isopropyl or tert. butyl 4-(3,4 -dichlorophenyl)-4-ketobutanoate is substantially complete. This, in turn, will often preferably require a period of at least about 18 hours when the reaction is most conveniently conducted at about room temperature (ca. 20° C.). Upon completion of this particular reaction step, the desired isopropyl or tertiary-butyl ester product is then easily isolated from the reaction mixture in a most conventional manner, viz., by first removing excess isopropylene or isobutylene gas via suitable evaporation or distillation techniques and then triturating the resulting distill and with saturated aqueous sodium bicarbonate solution to adjust the pH to a value that is slightly basic, followed by separation of the layers and subsequent evaporation of the dried organic layer to ultimately yield the desired branched-chain ester product. The latter product can then be further purified by means of column chromatography over silica gel, in accordance with standard techniques well-known to those skilled in the art.

The intermediate 4-ketobutanoic acid ester product obtained in step (a) is then reduced to the corresponding chiral 4-(3,4-dichlorophenyl)-(4R)-hydroxybutanoate ester compound in step (b) by using an appropriate asymmetric carbonyl-reducing agent that is capable of reducing a ketone in the presence of a carboxylic acid ester group. This category preferably includes, for the present purposes at hand, chiral reducing agents as the catalyst, viz., the optically-active oxazaborolidine compounds known as (S) -tetrahydro-1-methyl-3,3-diphenyl-1H, 3H-pyrrolo[1,2-c] [1,3,2]oxazaborole, (S)-tetrahydro-1,3,3-triphenyl-1H, 3H-pyrrolo[ 1,2-c][1,3,2]oxazaborole and (S)-tetrahydro-1-n -butyl-3,3-diphenyl-1H, 3H-pyrrolo[1,2-c][1,3,2]oxazaborole when used in conjunction with borane or borane-dimethyl sulfide complex [see E. J. Corey et al., in the *Journal of Organic Chemistry*, Vol. 53, p. 2861 (1988) and D. J. Mathre et al., in the *Journal of Organic Chemistry*, Vol. 56, p. 751 (1991)]. Stoichiometric asymmetric carbonyl reducing agents for use in this connection include the optically-active compounds (R)-BINAL-H and (+)-diisopinocamphenylchloroborane (both known in the art as chiral reducing agents). In general, the reduction step is carried out in a reaction-inert polar or non-polar aprotic organic solvent at a temperature ranging from about +15° C. up to about 40° C., and preferably from about 0° C. to about 25° C. until the reduction reaction to form the desired (4R)-hydroxy compound, viz., the desired isopropyl or tert.-butyl 4-(3,4-dichlorophenyl) -(4R)-hydroxybutanoate intermediate, is substantially complete. Preferred polar or non-polar aprotic, organic solvents for use in this connection include acetonitrile, benzene, toluene and ethers like diethyl ether, diisopropyl ether, di-n-butyl ether, tetrahydrofuran, dioxane and 1,2-dimethoxyethane. A preferred embodiment involves the use of borane as the stoichiometric reductant with (S)-tetrahydro -1-methyl-3,3-diphenyl-1H, 3H-pyrrolo[1,2-c][1,3,2]oxazaborole as the catalyst, as previously indicated, wherein the reduction reaction step is preferably conducted in the presence of a cyclic ether such as dioxane or tetrahydrofuran. Although molar amounts of reactant and reagent are generally not critical in this connection, it is usually preferable in practice to employ an excess in moles of the starting keto compound with respect to both the borane reductant and the chiral oxazaborolidine catalyst, e.g., molar ratios ranging from about 20:12:1 to about 100:60:1 of keto substrate/reductant/catalyst have been found to be most useful in this particular connection. Upon completion of the reaction, the desired isopropyl or tert.-butyl 4-(3,4-dichlorophenyl)-(4R)-hydroxybutanoate intermediate is readily recovered from the reaction mixture, in accordance with conventional procedure or used as such (i.e., in situ) in the next reaction step without any further purification really being necessary.

The next step (c) in the overall process for preparing the desired (4S)-4-(3,4-dichlorophenyl)-3,4-dihydro-1(2H)-naphthalenone compound involves sulfonylating (i.e., esterifying) the (4R)-hydroxybutanoic acid ester compound obtained in step (b) with an organic sulfonyl halide of the formula RX, wherein R is methanesulfonyl, benzenesulfonyl or p-toluenesulfonyl and X is chlorine or bromine. This particular reaction is normally carried out in a reaction-inert organic solvent by treating said (4R)-hydroxy ester with at least an equivalent amount in moles of the organic sulfonyl halide under substantially anhydrous conditions and in the presence of a suitable amount, i.e., at least an equivalent amount, of an appropriate standard base. In general, the reaction is conducted at a temperature that is in the range of from about −20° C. up to about 40° C. for a period of time that is sufficient to ensure that sulfonylation of the (4R)-hydroxy group on the substrate molecule is substantially complete. The latter point usually requires a period of at least about 15 minutes and preferably a period of about one-half to about 24 hours, although it is often found most convenient in practice to carry out the reaction at ca. 0°–10° C. Although any inert organic solvent may be used for the reaction, it is generally most desirable to employ such solvents as aromatic hydrocarbons, halogenated lower hydrocarbons, lower dialkyl ethers, dioxane and tetrahydrofuran. Preferred aromatic hydrocarbons include benzene, toluene and xylene; preferred halogenated lower hydrocarbons include methylene chloride, chloroform, ethylene dichloride and s-tetrachlorethane; while preferred lower dialkyl ethers include diethyl ether, diisopropyl ether and di-n-butyl ether. Appropriate standard basic agents for use in this process include the alkali metal and alkaline-earth metal oxides, bicarbonates and carbonates, such as magnesium oxide, sodium bicarbonate, sodium carbonate and magnesium carbonate, as well as tertiary amines such as triethylamine, N,N-dimethylaniline, pyridine, picoline, lutidine, collidine and quinoline. It should be noted that the standard basic agent employed must be present in sufficient amount to neutralize the liberated hydrogen halide formed in the reaction. Triethylamine is the most preferred base because it can easily be removed from the reaction mixture in the form of the water-soluble triethylamine hydrohalide salt which forms as a byproduct of the reaction. Needless to say, the course of the reaction can easily be followed by means of thin-layer chromatography, thereby determining reaction times sufficient to provide complete reaction and at the same time avoiding unnecessary heating costs and excessive reaction time, which can often increase the level of unwanted by-product formation and thereby lower the desired yields. Upon completion of the reaction, the (4R)-methanesulfonyl, (4R)-benzenesulfonyl or (4R)-p-toluenesulfonyl derivative of the 4-(3,4-dichlorophenyl)-(4R)-hydroxybutanoate ester so prepared is usually most conveniently recovered from the reaction mixture by first quenching same with water and then collecting the separated organic layer therefrom, followed by evaporation of the solvent under reduced pressure to ultimately yield the desired sulfonyl derivative in substantially pure form. This product can also be used as such in the next reaction step without any further purification being necessary.

The fourth stage (d) of the overall multi-step process of the present invention involves subjecting the isopropyl or tert.-butyl (4R)-sulfonyloxybutanoic acid ester obtained in step (c) to a copper-coupling reaction with dilithium diphenyl(cyano)cuprate of the formula $\phi_2Cu(CN)Li_2$ in a reaction-inert aprotic organic solvent, such as a cyclic or lower dialkyl ether at a temperature ranging from about −80° C. up to about 20° C., to effect a stereochemical displacement of the organic (4R)-sulfonyloxy group of the (4R)-sulfonyloxybutanoic acid ester by the phenyl group of the dilithium diphenylcuprate reagent and so selectively form the corresponding isopropyl or tert.-butyl 4-(3,4 -dichlorophenyl)-(4R)-phenylbutanoate. Preferred cyclic ethers for use as reaction-inert aprotic organic solvents in this connection include tetrahydrofuran and dioxane, while preferred lower dialkyl ethers for the same purposes include methyl tert.-butyl ether, diethyl ether, di-isopropyl ether and di-n-butyl ether, etc. In a preferred embodiment, the molar ratio of (4R)-sulfonyloxybutanoic acid ester to dilithium diphenyl-(cyano)cuprate reagent will ordinarily vary from about 1:1 to about 1:3, respectively, with the most preferred molar ratios being in the neighborhood of about 1:2 for the present purposes at hand. In general, the stereospecific reaction is conducted at temperatures lying within the approximate range of −80° C. to 20° C. as aforesaid, with preferred temperatures usually being well-within the range of from about −70° C. to about −10° C. and most preferably, within the −55° C. to −10° C. range, at least until the stereospecific reaction is substantially complete. In practice, the latter step is usually accomplished in a time period that is preferably at least about two hours and even more preferably, within a period of time that is about five to 18 hours. Upon completion of the stereospecific phenylation reaction, the desired isopropyl or tert.-butyl 4-(3,4-dichlorophenyl)-(4R)-phenylbutanoate compound is readily recovered from the aforesaid reaction mixture by first quenching same with an ice/water mixture containing a weak acid, such as saturated aqueous ammonium chloride, to effect hydrolysis of the resulting reaction complex, followed by further stirring to effect a clear separation of the two phases and subsequent isolation of the desired product from the ethereal organic phase, with the latter step being preferably accomplished by means of evaporation of the solvent therefrom, followed by further purification of the residual oil via column chromatography on silica gel and subsequent elution with 5% ethyl acetate/n-hexane to afford the pure intermediate ester product, viz., the aforementioned isopropyl or tert.-butyl 4-(3,4 -dichlorophenyl)-(4R)-phenylbutanoate compound.

The fifth and final stage (e) of the multi-step process of this invention involves cyclizing the stereospecific (4R)-phenylated n-butanoic acid ester obtained in step (d), viz., isopropyl or tert.-butyl 4-(3,4-dichlorophenyl)-(4R)-phenylbutanoate, in a reaction-inert aprotic organic solvent in the presence of a protic or Lewis acid catalyst at a temperature ranging from about −20° C. up to about 180° C., until the intramolecular ring-closure of the intermediate 4 -(3,4-dichlorophenyl)-(4R)-phenylbutanoic acid (which is first formed in situ) is substantially complete to thus yield the desired final product, viz., (4S)-4-(3,4 -dichlorophenyl) -3,4-dihydro-1(2H) -naphthalenone, in a highly-optically pure form (and in a high yield). Preferred reaction-inert aprotic organic solvents for use in this connection include carbon disulfide, nitrobenzene, various nitroalkanes like nitromethane and nitroethane, aromatic hydrocarbon solvents such as benzene, toluene and xylene, as well as halogenated benzene compounds like o-dichlorobenzene and bromobenzene, in addition to various halogenated lower hydrocarbons such as methylene chloride, ethylene dichloride, trichloroethylene, s-tetrachlorethane and carbon tetrachloride, etc. Preferred protic or Lewis acid catalysts for use in the ring-closure reaction include sulfuric acid, trifluoromethanesulfonic acid, hydrofluoric acid, methanesulfonic acid, polyphosphoric acid, phosphorus pentoxide, aluminum chloride, phosphorus pentachloride, titanium tetrachloride and various acidic ion-exchange resins, with the most preferred members being the first four-named protic acids. In a preferred embodiment of this particular step, the molar ratio of stereospecific phenylated n-butanoic acid ester employed as starting material to acid catalyst is one that is in the range of from about 10:1.0 to about 1.0:90.0, with the most preferred phenylated n-butanoic acid ester/acid catalyst ratios ranging from about 1.0:1.0 to about 1.0:50.0. In practice, the reaction is preferably conducted at a temperature ranging from about 15° C. up to about 145° C., with the most preferred temperature range being between about 15°–100° C. In the case where the acid catalyst employed is a protic acid such as sulfuric acid, trifluoromethanesulfonic acid or methanesulfonic acid, the preferred temperature range is generally between about 15°–100° C., as aforesaid, and most preferably, between about 20°–100° C. In the case where the protic acid employed is hydrofluoric acid, the preferred temperature range is generally between about 15°–100° C. as aforesaid, and most preferably, between about 15°–30° C. for the present purposes at hand. Upon completion of this reaction step, the desired (4S)-4-(3,4-dichlorophenyl)-3,4 -dihydro-1(2H)-naphthalenone compound is readily recovered from the reaction mixture in a conventional manner that is most common to these type reactions, viz., by first quenching the reaction mixture with ice, followed by basification of the aqueous medium so obtained and a further stirring of same to effect a separation of the two phases and the subsequent isolation of the product from the organic phase, with the latter step being preferably accomplished by means of evaporation of the solvent therefrom, followed by further purification of the resulting oily residue, preferably via column chromatography over silica gel, etc. In this way, the novel five-step process of this invention to prepare the new and valuable (4S)-4-(3,4-dichlorophenyl) -1(2H)-naphthalenone compound from the known 4-(3,4 -dichlorophenyl)-4-ketobutanoic acid is now essentially complete.

The 4-(3,4-dichlorophenyl)-4-ketobutanoic acid ultimate starting material required for carrying out the five-step method of production involved with the overall process of this invention is a known compound which can easily be synthesized by those skilled in the art, starting from common chemical agents and using conventional methods of organic synthesis. For instance, this particular compound is readily prepared by employing the method of E. A. Steck et al., as described in the *Journal of the American Chemical Society*, Vol. 75, p. 1117 (1953).

As previously indicated, the (4S)-4-(3,4 -dichlorophenyl)-3,4-dihydro-1(2H)-naphthalenone final product afforded by the multi-step process of this invention is a valuable intermediate that ultimately leads to the antidepressant agent known as sertraline or cis-(1S) (4S) -N-methyl-4-(3,4-dichlorophenyl)-1,2,3,4-tetrahydro-1-naphthaleneamine by methods disclosed in the previously discussed prior art. More specifically, (4S)-(3,4 -dichlorophenyl)-3,4-dihydro-1(2H)-naphthalenone is first converted to (4S)-N-[4-(3,4-dichlorophenyl)-3,4-dihydro-1 (2H)-naphthalenylidine] methanamine and then finally to the desired cis-(1S) (4S)-

N-methyl-4-(3,4-dichlorophenyl) -1,2,3,4-tetrahydro-1-naphthaleneamine by the known methods of the prior art process, as earlier described by W. M. Welch, Jr. et al., in U.S. Pat. No. 4,536,518, as well as in the *Journal of Medicinal Chemistry*, Vol. 27, No. 11, p. 1508 (1984), for the corresponding series of compounds where the starting material is the racemic form of 4-(3,4 -dichlorophenyl)-1(2H)-naphthalenone. In the present instance, the optically-active ketone, viz., (4S)-4-(3,4 -dichlorophenyl)-1(2H)-naphthalenone, is first reductively aminated to give chiral cis-N-methyl-(3,4-dichlorophenyl) -1,2,3,4-tetrahydro-1-naphthaleneamine and the latter product is then separated by chromatographic means to ultimately yield the desired final medicinal product which is sertraline.

Hence, the novel process of the present invention now provides the new and valuable (4S)-enantiomer known as (4S) -4-(3,4-dichlorophenyl)-3,4-dihydro-1(2H)-naphthalenone, as discussed above, in pure form and in high yield by a unique five-step method. This, in turn, allows for a major improvement in the overall synthesis of sertraline by permitting use of the previously-undisclosed asymmetric route, whereby some of the hereinbefore discussed disadvantages of the known prior art method are now largely circumvented.

EXAMPLE 1

A well-stirred mixture consisting of 5.0 g (0.02 mole) of 4-(3,4-dichlorophenyl)-4-ketobutanoic acid [E. A. Steck et al., *Journal of the American Chemical Society*, Vol. 75, p. 1117 (1953)] dispersed in 100 mL of 1,2-dichlorobenzene (o-dichlorobenzene), which also contained 1.0 mL of tert.-butanol and 1.0 mL of concentrated sulfuric acid, was treated with 31 g (0.5 mole) of gaseous isobutylene that had been condensed into the mixture with the aid of a dry-iced cold finger. The resulting reaction mixture was then stirred at room temperature (ca. 20° C.) for a period of 18 hours. Upon completion of this step, the excess isobutylene was removed by means of distillation and the remaining liquid constituting the distill and was subsequently mixed with 100 mL of saturated aqueous sodium bicarbonate solution and stirred at that point for a period of 30 minutes to afford a media having a pH of 8.0. The two liquid layers were then separated, and the organic layer was saved and subsequently dried over anhydrous magnesium sulfate. After removal of the drying agent by means of filtration and the solvent by means of evaporation under reduced pressure, there were obtained 8.31 g of crude tert.-butyl ester product in the form of the residual oil. Purification of the latter material was then accomplished by means of column chromatography on silica gel (90 g), using a 10% ethyl acetate/n-hexane solution as the eluant to ultimately give 5.64 g (92%) of pure tert.-butyl 4-(3,4-dichlorophenyl)-4-ketobutanoate as a clear colorless oil. The pure product was characterized by means of nuclear magnetic resonance data, in addition to elemental analysis.

NMR Data: $^{13}$C-NMR (CDCl$_3$) 196.3, 171.9, 137.7, 136.3, 133.4, 130.8, 130.1, 127.1, 80.9, 33.5, 29.3, 28.1.

Anal. Calcd. for C$_{14}$H$_{16}$Cl$_2$O$_3$: C, 55.46; H, 5.32.

Found: C, 55.32; H, 5.29.

EXAMPLE 2

A solution consisting of 3.0 g (0.009 mole) of tert.-butyl 4-(3,4-dichlorophenyl)-4-ketobutanoate (the product of Example 1) dissolved in 3.0 mL of tetrahydrofuran was added separately, but simultaneously with 5.94 mL of a 1M solution of borane (0.00594 mole) dispersed in tetrahydrofuran via a double syringe pump over a 40-minute period to a well-stirred solution consisting of 137 mg (0.0005 mole) of (S) -tetrahydro-1-methyl-3,3-diphenyl-1H, 3H-pyrrolo[1, 2c] [1,3,2]oxazaborole [E. J. Corey et al., *Journal of Organic Chemistry*, Vol. 53, p. 2861 (1988)] dissolved in 6 mL of tetrahydrofuran at 0° C. Upon completion of the double concurrent addition step, the resulting reaction mixture was stirred at room temperature (ca. 20° C.) for a period of 30 minutes and then quenched with 9.6 mL of methanol, followed by further stirring at the latter point for another 30-minute period. The organic solvents were next removed from the quenched reaction mixture under vacuum, followed by the addition of 30 mL of methylene chloride to the resultant residue to afford a new organic phase. The latter was then washed twice with fresh 25 mL-portions of a phosphate pH 4 buffer and then once with 25 mL of water, and thereafter dried over anhydrous magnesium sulfate. After removal of the drying agent by means of suction filtration and the solvents by means of evaporation under reduced pressure, there were finally obtained 3.17 g (105%) of crude tert.-butyl 4-(3,4-dichlorophenyl)-(4R)-hydroxybutanoate. This material was used as such in the next reaction step without any further purification being necessary.

EXAMPLE 3

To a well-stirred solution consisting of 2.96 g (0.0097 mole) of tert.-butyl 4-(3,4-dichlorophenyl)-(4R)-hydroxybutanoate (the product of Example 2) dissolved in 48 mL of methylene chloride containing 2.02 mL (0.014 mole) of triethylamine at 0° C. there was slowly added 1.04 mL (0.0106 mole) of methanesulfonyl chloride in a dropwise manner. Upon completion of this step, the resulting reaction mixture was stirred at room temperature (ca. 20° C.) for a period of 20 minutes and then quenched with 25 mL of ice-cold water, with the resultant phases being allowed to separate. The separated organic layer was next washed with 25 mL of 3N aqueous hydrochloric acid and then with 25 mL of saturated aqueous sodium bicarbonate and 25 mL of brine, followed by drying over anhydrous magnesium sulfate. After removal of the drying agent by means of suction filtration and the solvent by means of evaporation under reduced pressure, there were finally obtained 3.90 g (97%) of crude (4R)-mesyl ester, i.e., tert.-butyl 4-(3,4-dichlorophenyl)-(4R) -methanesulfonyloxybutanoate, which was used as such in the next reaction step (viz., the copper-coupling step) without any further purification being necessary.

EXAMPLE 4

A well-stirred suspension consisting of 867 mg (0.00968 mole) of cuprous cyanide in 30 mL of diethyl ether at −20° C. was treated in a dropwise manner with 20 mL of a 0.96M solution of phenyllithium (0.0192 mole) in diethyl ether during the course of a ten-minute addition period to generate dilithium diphenyl(cyano)cuprate [φCu(CN)Li$_2$] in situ. Upon completion of this step, the reaction mixture was stirred at −20° C. for a period of 30 minutes and then at 0° C. for another period of 30 minutes before finally being cooled to −45° C. At this point, a solution consisting of 2.0 g (0.00484 mole) of tert.-butyl 4-(3,4-dichlorophenyl) -(4R)-methanesulfonyloxybutanoate (the product of Example 3) dissolved in 5 mL of diethyl ether was next added to the stirred reaction mixture containing dilithium diphenyl(cyano)cuprate over a ten-minute period and the resulting mixture was then stirred at −45° C. for a period of 16 hours. The final reaction mixture so obtained was then quenched with 90 mL of saturated aqueous ammonium chloride solution and 90 g of ice, and thereafter stirred for a period of one hour. The two phases which formed at this point were then separated, and the aqueous layer was again extracted with a fresh portion of diethyl ether. The two separated ethereal extracts were next combined and subsequently dried over anhydrous magnesium sulfate, filtered and the resulting filtrate thereafter concentrated in vacuo to afford 2.15 g of a pale yellow oil. Purification of the latter material was then accomplished by means of column chromatography on silica gel (63 g), using a 5% ethyl acetate/n-hexane solution as the eluant to ultimately afford 1.25 g (70%) of pure tert.-butyl 4-(3,4 -dichlorophenyl)-(4R)-phenylbutanoate in the form of a colorless oil, $[\alpha]_D^{25}$–4.00 (c=1.15, benzene).

Anal. Calcd. for $C_{20}H_{22}Cl_2O_2$: C, 65.76; H, 6.07.

Found: C, 65.82; H, 5.92.

EXAMPLE 5

To a well-stirred solution consisting of 668 mg (0.00183 mole) of tert.-butyl 4-(3,4-dichlorophenyl)-(4R)-phenylbutanoate (the product of Example 4) dissolved in 5.0 mL of benzene at ambient temperature (ca 20° C.) there were slowly added 5.0 mL (0.056 mole) of trifluoromethanesulfonic acid. The resulting reaction mixture was then stirred and heated to 70° C. and maintained at that point for a period of two hours. Upon completion of this step, the stirred reaction mixture was cooled to ambient temperature and then quenched onto 20 g of ice, followed by an adjustment of the pH value of the resultant aqueous medium to a new value of pH 13 via the addition thereto of 15 mL of 4S aqueous sodium hydroxide solution. At this point, the two layers were separated and the aqueous layer was next extracted with an equal volume of methylene chloride. The two organic layers were then combined and subsequently dried over anhydrous magnesium sulfate. After removal of the drying agent by means of suction filtration and the solvent by means of evaporation under reduced pressure, there was obtained 612 mg of a light yellow oil as the residue. Purification of the latter material by means of column chromatography over silica gel (18 g), using a 15% ethyl acetate/n-hexane solution as the eluant, then gave 500 mg (94%) of (4S)-4 -(3,4-dichlorophenyl)-3,4-dihydro-1(2H)-naphthalenone, $[\alpha]_D^{25°}$+55.7° (c=1.01, acetone), which amounted to a 93:7 ratio of enantiomers or an optical purity of 86% when expressed in terms of the percent amount of enantiomeric excess (% ee).

Anal. Calcd. for $C_{16}H_{12}Cl_2O$: C, 66.00; H, 4.15.

Found: C, 65.97; H, 4.15.

EXAMPLE 6

A suspension of 2.92 g (0.008 mole) of tert.-butyl 4 -(3,4-dichlorophenyl)-(4R)-phenylbutanoate (the product of Example 4) in 30 mL of 30% aqueous sulfuric acid and 20 mL of 98% acetic acid is heated to 80° C. for a period of 15 minutes, then at 60° C. for a period of five hours and finally kept at room temperature (ca. 20° C.) for a period of 16 hours. The resulting acidic solution is subsequently concentrated in vacuo to an oily residue, which is then dissolved in saturated aqueous sodium bicarbonate solution and thereafter treated with 3N hydrochloric acid to give a precipitate. The solid product is then recovered by means of suction filtrate and recrystallized from ethanol/petroleum ether after treatment with activated charcoal to finally afford pure 4-(3,4-dichlorophenyl)-(4R)-butanoic acid, identical in every respect with the product of Example 7 as hereinafter described.

EXAMPLE 7

To a well-stirred solution of 690 mg (0.00234 mole) of 4-(3,4-dichlorophenyl)-(4R)-phenylbutanol (the product of Preparation F) dissolved in 45 mL of acetone at ambient temperature, there were added 6.0 mL of Jones' reagent. The resulting reaction mixture was next stirred for a period of two hours and then quenched via the addition thereto of 5.0 mL of isopropanol. After stirring the quenched reaction mixture for a period of 30 minutes, the solvents already present therein were subsequently removed under vacuum to afford a green solid product as the residue. The latter product was then taken up in water and extracted twice with separate 25 mL-portions of methylene chloride. The two organic phases were next combined and subsequently dried over anhydrous magnesium sulfate. After removal of the drying agent by means of suction filtration and the solvent by means of evaporation under reduced pressure, there was finally obtained 689 mg (95%) of pure 4-(3,4 -dichlorophenyl)-(4R)-phenylbutanoic acid in the form of a colorless oil, $[\alpha]_D^{25°}$–12.75° (c=1.16, benzene). The pure product was further characterized by means of nuclear magnetic resonance data.

NMR Data: $^1$HNMR (CDCl$_3$) δ 6 7.36–7.06 (m, 8H), 3.92 (t, J=7Hz, 1H) , 2.43–2.22 (m, 4H) .

EXAMPLE 8

To a well-stirred solution consisting of 689 mg (0.00223 mole) of 4-(3,4-dichlorophenyl)-(4R)-phenylbutanoic acid (the product of Example 7) dissolved in 5.0 mL (0.056 mole) of benzene at ambient temperature, there were added 5.0 mL of trifluoromethanesulfonic acid. The resulting reaction mixture next heated at 70° C. for a period of two hours, and then cooled and quenched with 20 g of ice. The pH of the quenched solution was then adjusted to pH 12 by adding 14.5 mL of 4S aqueous sodium hydroxide thereto. The resulting basic solution was next extracted twice with separate 30 mL-portions of methylene chloride, and the two organic phases were then combined and dried over anhydrous magnesium sulfate. After removal of the drying agent by means of suction filtration and the solvent by means of evaporation under reduced pressure, there was obtained 692 mg of crude product in the form of a light yellow oil which soon began to crystallize on standing. The solid product was then collected by means of suction filtration and subsequently chromatographed on a silica gel column, using ethyl acetate/hexane as the eluant to finally give 592 mg (91%) of pure (4S)-4-(3,4-dichlorophenyl)-3,4-dihydro-1(2H)-naphthalenone in the form of a white crystalline solid, $[\alpha]_D^{25°}$+ 58.3 (c=1.01, acetone). This amounted to an optical purity of 88.6% when expressed in terms of the percent amount of enantiomeric excess (% ee). The pure product was further characterized by means of nuclear magnetic resonance data, mass spectroscopy and infrared absorption data, in addition to elemental analysis, and was found to be identical in every respect with the product of Example 8.

Anal. Calcd. for $C_{16}H_{12}Cl_2O$: C, 66.00; H, 4.15.

Found: C, 66.20; H, 3.91.

PREPARATION A

To a well-stirred solution consisting of 100 g (0.40 mole) of racemic or (±)-4-(3,4-dichlorophenyl)-4-ketobutanoic [E. A. Steck et al., *Journal of the American Chemical Society*, Vol. 75, p. 1117 (1953)] dissolved in 610 mL of 1N aqueous sodium hydroxide at ambient temperature (ca. 20° C.), there were added 8.53 g (0.225 mole) of powdered sodium borohydride in small divided portions while the temperature of the mixture was always maintained below 35° C. Upon completion of this step, the resulting aqueous basic reaction mixture (pH>10) was next stirred at ambient temperatures for a period of 18 hours and then further cooled to a temperature below 5° C. prior to being acidified with 73 mL of concentrated hydrochloric acid to pH 1.0. The acidified aqueous solution was next extracted twice with separate 500 mL-portions of methylene chloride, and the combined organic extracts were then successively washed with two-150 mL portions of water and two-50 mL portions of brine, followed by drying in the usual manner over anhydrous magnesium sulfate. After removal of the drying agent by means of suction filtration, the methylene chloride solution containing (±)-4-(3,4-dichlorophenyl)-4-hydroxybutanoic acid was added to a well-stirred solution consisting of 69.68 g (0.422 mole) of D-(+)-ephedrine dissolved in 1660 mL of methylene chloride at ambient temperature, and then seeded and allowed to stir overnight at this same temperature for a period of ca. 16 hours. The white solid ephedrine salt so obtained was then recovered from the aforesaid reaction mixture by means of suction filtration and washed on the filter funnel with 100 mL of fresh methylene chloride to afford (after first drying in vacuo to constant weight) 108.6 g of the diastereoisomeric D-(+)-ephedrine salt of (±)-4-(3, 4-dichlorophenyl)-4-hydroxybutanoic acid, $[\alpha]_D^{25°}+22.6°$ (c=1, methanol).

The above isolated diastereoisomeric salt (108.6 g) was next dissolved in 4000 mL of methylene chloride and the resulting solution was concentrated in vacuo to a total volume of 2100 mL. A white solid product soon precipitated and the suspension thus obtained was further stirred at this point for a period of ca. 16 hours. The precipitated salt product was then collected by means of suction filtration and dried to constant weight to yield 46.4 g of a white solid, $[\alpha]_D^{25°}+30.2$ (c=1, methanol). This fraction was combined with 25.3 g of a salt product having an optical rotatory value of $[\alpha]_D^{25°}+30.7°$ (c=1, methanol) that had been obtained from a previous preparation, and the combined fractions were dissolved in 9000 mL of fresh methylene chloride and subsequently concentrated in vacuo to a total volume of 1450 mL. A white solid product again soon precipitated from solution and was thereafter stirred as a suspension at this point for a period of ca. 16 hours. The thus precipitated salt product was next collected by means of suction filtration as before and washed on the filter funnel with 200 mL of fresh methylene chloride to ultimately yield (after first drying in vacuo to constant weight) 63 g of a white solid product that was the pure D-(+)-ephedrine salt of 4-(3,4-dichlorophenyl)-4(4R)-hydroxybutanoic acid, $[\alpha]_D^{25°}+29.8°$ (C=1, methanol).

The above isolated pure diastereoisomeric salt (56 g) was next dissolved in 122 mL of water, which also contained 110 mL of methylene chloride and 91 mL of concentrated hydrochloric acid, and the resulting mixture was stirred at ambient temperature for a period of one hour and then heated to 45° C. for a period of 1.75 hours. Upon completion of this step, the resulting reaction mixture was cooled to ambient temperature once again, and 130 mL of water and 130 mL of methylene chloride were subsequently added thereto, followed by filtration of the final mixture through celite. The two phases of the resulting filtrate were next separated, and the aqueous phase was extracted with fresh methylene chloride, which extract was then combined with the saved organic phase. The combined organic extracts were then successively washed with 130 mL of saturated aqueous sodium bicarbonate and 130 mL of water and thereafter dried over anhydrous magnesium sulfate. After removal of the drying by means of filtration and the solvent by means of evaporation under reduced pressure, there were finally obtained 30.1 g of pure chiral 5-(3,4-dichlorophenyl)-dihydro-2(3H)-furanone in the form of a white solid, m. p. 54°–55° C.; $[\alpha]_D^{25°}+12.3°$ (c=1, methanol).

PREPARATION B

A well-stirred suspension consisting of 1.53 g (0.04 mole) of lithium aluminum hydride in 16 mL of tetrahydrofuran was cooled in an ice-bath under a dry nitrogen atmosphere and treated with 10 g (0.0403 mole) of the chiral lactone product of Preparation A dissolved in 48 mL of tetrahydrofuran, with the latter solution being added in a dropwise manner to the aforesaid suspension. The reaction mixture was then stirred for a period of one hour in the ice bath, followed by stirring at 25° C. for a period of one hour and then at 60° C. for a period of 1.5 hours. Upon completion of this step, the reaction mixture was cooled and then quenched with 1.53 mL of water, 1.53 mL of 15% aqueous sodium hydroxide and finally with 4.6 mL of water. At this point, 30 mL of tetrahydrofuran were added and stirring was continued for a period of 16 hours. The final reaction mixture thus obtained was next filtered through magnesium sulfate under vacuum and the solvent remaining in the mixture was thereafter removed by means of evaporation under reduced pressure to ultimately afford 10.33 g of 4-(3,4-dichlorophenyl)-(4R)-hydroxybutanol in the form of a white solid, $[\alpha]_D^{25°}+36.7°$ (c=1.76, acetone). The pure product was further characterized by means of nuclear magnetic resonance data and mass spectroscopy, in addition to elemental analysis.

Anal. Calcd. for $C_{10}H_{12}Cl_2O_2$: C,51.09, H, 5.14.

Found: C, 51.17; H, 5.12.

PREPARATION C

A well-stirred solution consisting of 10.33 g (0.0041 mole) of 4-(3,4-dichlorophenyl)-(4R)-hydroxybutanol (the product of Preparation B) and 5.48 g (0.0806 mole) of imidazole dissolved in 93 mL of dimethylformamide was cooled in a ice bath under a dry nitrogen atmosphere and treated with 6.99 g (0.046 mole) of tert.-butyl dimethylsilyl chloride, which was added in one portion. Stirring was continued for a period of 18 hours, during which time the ice bath was allowed to melt under its own integrity. The resulting reaction mixture was then quenched inversely into 1000 mL of water and extracted four times with separate 100 mL-portions of hexane. The combined organic layers were next washed with two-200 mL portions of water and dried over anhydrous magnesium sulfate. After removal of the drying agent by means of suction filtration and the solvent by means of evaporation under reduced pressure, there were obtained 15.25 g of crude product in the form of a colorless oil. The latter product was then chromatographed on a silica gel column, using ethyl acetate/hexane (1:3 by volume) as the eluant to finally yield 13.85 g (98%) of pure tert.-butyl dimethylsilyl 4-(3,4-dichlorophenyl)-(4R)-hydroxybutyl ether in the form of a colorless oil, $[\alpha]_D^{25°}+21.49°$ (c=1.24, acetone). The pure product was further characterized by means of nuclear magnetic resonance data, mass spectroscopy and infrared absorption data.

PREPARATION D

To a well-stirred solution consisting of 1.74 g (0.00498 mole) the monosilylated diol product of Preparation C dissolved in 24 mL of methylene chloride that had been cooled in an ice/salt bath, there was added 1.04 mL (0.00748 mole) of triethylamine in a dropwise manner, followed by 0.535 mL (0.00548 mole) of methanesulfonyl chloride in the same fashion. Upon completion of this step, the resulting reaction mixture was stirred at ice/salt bath temperatures for a period of 15 minutes and then quenched with 25 mL of ice-cold water, with the resultant phases thereafter being allowed to separate. The separated organic layer was next washed with 12 mL of cold 10% cold aqueous hydrochloric acid and then with 12 mL of saturated aqueous sodium bicarbonate, followed by 25 mL of saturated aqueous sodium chloride (brine) and then dried over anhydrous magnesium sulfate. After removal of the drying agent by means of suction filtration and the solvent by means of evaporation under reduced pressure, there were finally obtained 2.15 g (97%) of the desired (4R)-mesylester, viz., tert.-butyl dimethylsilyl 4-(3,4-dichlorophenyl)-(4R)-methanesulfonyloxybutanoate, in the form of a colorless oil, which was used as such in the next reaction step without any further purification being necessary. The aforesaid ester product was characterized by means of nuclear magnetic resonance data and mass spectroscopy.

PREPARATION E

A well-stirred suspension consisting of 572 mg. (0.00639 mole) of cuprous cyanide in 25.5 mL of diethyl ether at $-20°$ C. was treated in a dropwise manner with 8.19 mL of a 1.56M solution of phenyllithium (0.01278 mole) in diethyl ether during the course of a ten-minute addition period in order to generate dilithium diphenyl(cyano)cuprate [$(\phi)_2Cu(CN)Li_2$] in situ. Upon completion of this step, the reaction mixture was stirred at $-20°$ C. for a period of 20 minutes and then at $0°$ C. for a period of 30 minutes (a light yellow precipitate formed at this point) before finally being cooled to $-50°$ C. At this point, a solution consisting of 1.415 g (0.00319 mole) of tert.-butyl dimethylsilyl 4-(3,4-dichlorophenyl)-(4R)-methanesulfonyloxybutanoate (the product of Preparation D) dissolved 3.2 mL of diethyl ether was next added dropwise to the stirred reaction mixture containing dilithium diphenyl(cyano)cuprate over an eight-minute period and the resulting reaction mixture was then stirred at $-25°$ C. for a period 18 hours, followed by further stirring at ambient temperature for a period of 5.5 hours. The final reaction mixture so obtained was next quenched inversely onto 60 g of ice and 60 mL of aqueous saturated ammonium chloride solution, and thereafter stirred for a period of one hour. The two phases which formed at this point were then separated, and the aqueous phase was further extracted with two-50 mL portions of pure diethyl ether. The two separated ethereal extracts were next combined and subsequently dried over anhydrous magnesium sulfate, filtered and the resulting filtrate subsequently concentrated in vacuo to afford 1.92 g of a pale yellow oil. Purification of the latter material was then accomplished by means of column chromatography on silica gel, using ethyl acetate/hexane (1:99 by volume) as the eluant to ultimately afford 911 mg. (70%) of pure tert.-butyl dimethylsilyl 4-(3,4-dichlorophenyl)-(4R)-phenylbutanoate in the form of a colorless oil, $[\alpha]_D^{25°}$ $-4.81°$ (c=1.06, $CDCl_3$). The pure product was further characterized by means of nuclear magnetic resonance data and mass spectroscopy.

PREPARATION F

A solution consisting of 911 mg. (0.00223 mole) of the diarylsilylated product of Preparation E dissolved in 12 mL of glacial acetic acid, 4.0 mL of tetrahydrofuran and 4.0 mL of water was stirred at ambient temperature for a period of 24 hours. Upon completion of this step, the solvents were next removed under vacuum and 10 mL of 5% aqueous sodium bicarbonate and 10 mL methylene chloride were subsequently added to the residue. The resulting aqueous phase was then thoroughly extracted, and the separated organic phase was thereafter saved and subsequently dried over anhydrous magnesium sulfate. After removal of the drying agent by means of suction filtration and the solvent by means of evaporation under reduced pressure, there was finally obtained 838 mg. of residual product in the form of a colorless oil. Chromatography of the latter material on silica gel, using ethyl acetate/hexane (1:3 by volume) as the eluant, then ultimately gave 690 mg. (91%) of pure 4-(3,4-dichlorophenyl)-(4R)-phenylbutanol, $[\alpha]_D^{25°}$ $-2.71°$ (c=1.36, acetone). The pure product was further characterized by means of nuclear magnetic resonance data and mass spectroscopy.

I claim:

1. A process for preparing the (4S)-enantiomer of 4-(3,4-dichlorophenyl)-3,4-dihydro-1(2H)-naphthalenone in a highly-optically pure form, starting from 4-(3,4-dichlorophenyl)-4-ketobutanoic acid, which comprises the sequential series of steps that involve:

(a) first esterifying 4-(3,4-dichlorophenyl)-4-ketobutanoic acid with isopropylene or isobutylene in a reaction-inert aprotic organic solvent in the presence of an acidic catalyst to form the corresponding isopropyl or tert.-butyl 4-(3,4-dichlorophenyl)-4-ketobutanoate;

(b) reducing the 4-ketobutanoic acid ester obtained in step (a) with an appropriate asymmetric carbonyl reducing agent in a reaction-inert polar or non-polar aprotic organic solvent at a temperature ranging from about $-15°$ C. up to about $40°$ C., until the reduction reaction to form the desired chiral isopropyl or tert.-butyl 4-(3,4-dichlorophenyl)-(4R)-hydroxybutanoate intermediate is substantially complete;

(c) sulfonylating the (4R)-hydroxybutanoic acid ester compound formed in step (b) with an organic sulfonyl halide of the formula RX, wherein R is methanesulfonyl, benzenesulfonyl or p-toluenesulfonyl and X is chlorine or bromine, in a reaction-inert organic solvent at a temperature ranging from about $-20°$ C. up to about $+40°$ C. in the presence of a standard base to yield the corresponding isopropyl or tert.-butyl 4-(3,4-dichlorophenyl)-(4R)-sulfonyloxybutanoate;

(d) subjecting the (4R)-sulfonyloxybutanoic acid ester obtained in step (c) to a copper-coupling reaction with dilithium diphenyl(cyano)cuprate of the formula $\phi_2Cu(CN)Li_2$ in a cyclic or lower dialkyl ether at a temperature ranging from about $-80°$ C. up to about $20°$ C. to effect a stereochemical displacement of the organic (4R)-sulfonyloxy group of the (4R)-sulfonyloxybutanoic acid ester by the phenyl group of the dilithium diphenylcuprate reagent and so selectively form the corresponding isopropyl or tert.-butyl 4-(3,4-dichlorophenyl)-(4R)-phenylbutanoate ester; and (e) thereafter cyclizing the stereospecific (4R)-phenylated n-butanoic acid ester product of step (d) in a reaction-inert aprotic organic solvent in the presence of a protic or Lewis acid catalyst at a temperature ranging from about $-20°$ C. up to about $180\sqrt{}$ C. to finally yield the desired (4S)-4-(3,4-dichlorophenyl)-3,4-dihydro-1(2H)-naphthalenone compound in a highly optically-pure form.

2. A process as claimed in claim 1 wherein the ester-forming reagent employed in step (a) is isobutylene.

3. A process as claimed in claim 1 wherein the reaction-inert aprotic organic solvent employed in step (a) is a chlorinated aromatic hydrocarbon solvent.

4. A process as claimed in claim 3 wherein the chlorinated aromatic hydrocarbon solvent is 1,2-dichlorobenzene.

5. A process as claimed in claim 1 wherein the acidic catalyst employed in step (a) is concentrated sulfuric acid.

6. A process as claimed in claim 1 wherein the asymmetric carbonyl reducing agent employed in step (b) is borane admixed with (S)-tetrahydro-1-methyl-3,3-diphenyl-1H,3H-pyrrolo[1,2-c][1,3,2]oxazaborole.

7. A process as claimed in claim 1 wherein the aprotic organic solvent employed in step (b) is tetrahydrofuran.

8. A process as claimed in claim 1 wherein the reduction reaction in step (b) is conducted at a temperature ranging from about 0° C. up to about 25° C.

9. A process as claimed in claim 1 wherein the sulfonyl halide employed as the sulfonylating agent in step (c) is methanesulfonyl chloride.

10. A process as claimed in claim 1 wherein the reaction-inert organic solvent employed in step (c) is a chlorinated lower hydrocarbon solvent.

11. A process as claimed in claim 1 wherein the chlorinated lower hydrocarbon solvent is methylene chloride.

12. A process as claimed in claim 1 wherein the standard base employed in step (c) is an organic tertiary-amine.

13. A process as claimed in claim 12 wherein the organic tertiary-amine is triethylamine.

14. A process as claimed in claim 1 wherein the ethereal solvent employed in step (d) is tetrahydrofuran.

15. A process as claimed in claim 1 wherein the ethereal solvent employed in step (d) is a lower dialkyl ether.

16. A process as claimed in claim 15 wherein the lower dialkyl ether is diethyl ether.

17. A process as claimed in claim 1 wherein the reaction-inert aprotic organic solvent employed in step (e) is an aromatic hydrocarbon solvent.

18. A process as claimed in claim 17 wherein the aromatic hydrocarbon solvent is benzene.

19. A process as claimed in claim 17 wherein the aromatic hydrocarbon solvent is toluene.

20. A process as claimed in claim 1 wherein the acid catalyst employed in step (e) is a protic acid.

21. A process as claimed in claim 20 wherein the protic acid is trifluoromethanesulfonic acid.

22. A compound selected from the group consisting of 4-(3,4-dichlorophenyl)-(4R)-phenylbutanoic acid and the isopropyl and tert.-butyl esters of said acid.

23. A compound as claimed in claim 22 which is the tert.-butyl ester of said acid.

24. An isopropyl or tert.-butyl ester of 4-(3,4-dichlorophenyl)-(4R)-hydroxybutanoic acid and the (4R)-methanesulfonyl, (4R)-benzenesulfonyl and (4R)-p-toluenesulfonyl derivatives thereof.

25. A compound as claimed in claim 24 which is the tert.-butyl ester of the (4R)-methanesulfonyl derivative.

* * * * *